(12) United States Patent
Jones

(10) Patent No.: US 10,994,152 B2
(45) Date of Patent: May 4, 2021

(54) DERMATOLOGICAL TREATMENT APPARATUS

(71) Applicant: iPulse Limited, Swansea (GB)

(72) Inventor: Stuart Terry Jones, Swansea (GB)

(73) Assignee: iPulse Limited, Swansea (GB)

( * ) Notice: Subject to any disclaimer, the term of this patent is extended or adjusted under 35 U.S.C. 154(b) by 62 days.

(21) Appl. No.: 16/332,741

(22) PCT Filed: Sep. 12, 2017

(86) PCT No.: PCT/GB2017/052673
§ 371 (c)(1),
(2) Date: Mar. 12, 2019

(87) PCT Pub. No.: WO2018/046966
PCT Pub. Date: Mar. 15, 2018

(65) Prior Publication Data
US 2019/0217120 A1 Jul. 18, 2019

(30) Foreign Application Priority Data

Sep. 12, 2016 (GB) ..................... 1615444

(51) Int. Cl.
*A61N 5/06* (2006.01)
*A61B 18/20* (2006.01)
(Continued)

(52) U.S. Cl.
CPC .......... *A61N 5/0616* (2013.01); *A61B 18/203* (2013.01); *A61B 2018/0047* (2013.01);
(Continued)

(58) Field of Classification Search
CPC .......... A61N 5/0616; A61N 2005/0644; A61N 2005/0655; A61N 2005/0667;
(Continued)

(56) References Cited

U.S. PATENT DOCUMENTS 5,137,018 A    8/1992  Chuprikov et al.
2004/0225339 A1 * 11/2004  Yaroslavsky .......... A61N 5/062
                                                              607/88

FOREIGN PATENT DOCUMENTS

CH    410212 A    3/1966
CH    410213 A    3/1966
(Continued)

OTHER PUBLICATIONS

International Search Report and Written Opinion for International Application No. PCT/GB2017/052673, dated Mar. 15, 2018, 9 pages.
(Continued)

*Primary Examiner* — Rex R Holmes
(74) *Attorney, Agent, or Firm* — Troutman Pepper Hamilton Sanders LLP; Ryan A. Schneider

(57) ABSTRACT

The present invention relates to a dermatological treatment apparatus. Such dermatological treatments include but are not limited to hair removal, treatment of acne and lesions and also skin rejuvenation. The apparatus comprises a housing; a light emitting source provided in the housing arranged to emit light energy along an energy pathway to external of the device; and a filter arrangement positioned in the energy pathway having at least a first and a second light energy filtering portion together combining to span across the energy pathway for filtering the light energy passing to external of the device.

20 Claims, 2 Drawing Sheets

(51) Int. Cl.
*A61B 18/00* (2006.01)
*A61B 18/18* (2006.01)

(52) U.S. Cl.
CPC ............... *A61B 2018/0091* (2013.01); *A61B 2018/00452* (2013.01); *A61B 2018/00476* (2013.01); *A61B 2018/1807* (2013.01); *A61N 2005/0644* (2013.01); *A61N 2005/0655* (2013.01); *A61N 2005/0667* (2013.01)

(58) Field of Classification Search
CPC ........ A61B 18/203; A61B 2018/00452; A61B 2018/0047; A61B 2018/00476; A61B 2018/0091; A61B 2018/1807
See application file for complete search history.

(56) References Cited

FOREIGN PATENT DOCUMENTS

| | | |
|---|---|---|
| DE | 2817908 A1 | 11/1979 |
| EP | 1857145 A1 | 11/2007 |
| EP | 2314246 A1 | 4/2011 |
| EP | 2724747 A1 | 4/2014 |
| WO | 99/58195 A1 | 11/1999 |

OTHER PUBLICATIONS

Search Report for GB Application No. 1615441.5, dated Feb. 15, 2017, 3 pages.

\* cited by examiner

DERMATOLOGICAL TREATMENT APPARATUS

CROSS-REFERENCE TO RELATED APPLICATIONS

This application is a § 371 national stage of International Application PCT/GB2017/052673, with an international filing date of 12 Sep. 2017, which claims the benefit under 35 USC § 119(a)-(d) and (f) of GB Patent Application Ser. No. 1615444.5, filed on 12 Sep. 2016. The entire contents and substance of each application is hereby incorporated by reference.

The present invention relates to a dermatological treatment apparatus. Such dermatological treatments include but are not limited to hair removal, treatment of acne and lesions and also skin rejuvenation.

Such systems include a light emitting source provided in a housing which emits pulses of light energy along an energy pathway onto the skin to be treated. A wide variety of systems exist including those that utilise intense pulse light (IPL) whereby a capacitor is discharged over a Xenon flash lamp such that the flash lamp emits an intense pulse of light energy. The wavelength of the light energy emitted ranges from close to 0 nm up to around 2000 nm. A problem exists in that light energy having a wavelength of less than approximately 500 nm is harmful to the skin and accordingly known apparatus utilises a filter to prevent such wavelength of the light energy passing onto the skin. Shorter wavelengths are highly absorbed in the skin, and have a shorter penetration depth. In addition UV wavelengths can be harmful to the skin causing burns and potential cancer. There are a variety of filters available including absorption filters which absorb the harmful wavelengths and also dichroic filters which reflect the harmful wavelengths. In both circumstances the harmful wavelength are prevented from contacting the skin.

A problem, however, exists with known filters. Known filters are susceptible to cracking due to mechanical stresses induced by the significant increase in temperature caused by the light energy. This problem increases as the average light power output increases. That is, for a fixed pulse energy, as the time between pulses is reduced, then the amount of light energy passing through the filter increases, and the time available for the filter to cool decreases. A reduction in the time between pulses is desirable for a home use product. This reduces overall treatment time therefore improving usability.

It is therefore desirable to provide an apparatus that can be used safely without requiring professional training that is easy to use quickly and effectively.

According to the present invention there is a light emitting apparatus for providing dermatological treatment comprising:

a housing;
a light emitting source provided in the housing arranged to emit light energy along an energy pathway to external of the device;
a filter arrangement positioned in the energy pathway having at least a first and a second light energy filtering portion together combining to span across the energy pathway for filtering the light energy passing to external of the apparatus.

It will be appreciated that more than two energy filtering portions may be utilised. The light filtering portions of the filter arrangement preferably have a cut-on value in the range of 470-650 nm, and even more preferably 510 nm.

The cut-on value means the value below which wavelengths of light are prevented from passing through.

The light emitting device may be an Intense Pulsed Light (IPL) apparatus. The light source is beneficially a flash lamp, wherein a suitable flash lamp is a xenon flash lamp.

The filter arrangement may be termed an absorption filter, and/or a high pass filter.

A significant benefit found to be associated with the present invention is that the apparatus can be run at a higher power output and at a reduced pulse separation, i.e. a reduced time between each pulse of light energy because the filter arrangement can withstand higher temperatures as the thermally induced stress in the light filtering portions is reduced. A benefit of this is it allows the device to be used in a so called "glide" mode whereby the device can be moved across the skin and the light emitting source can emit a series of pulses improving the speed of treatment.

By providing multiple light energy filtering portions, the stress experienced by each portion due to the heat generated is reduced. The increased heat associated with increased power and faster operation is accommodated by the first and multiple filter portions and thus the filter arrangement as a whole can withstand higher energy throughput. Prior art single piece filters are subject to higher stresses and tend to crack under such operating parameters.

The at least first and second light filtering portions may be positioned in a side by side configuration. The at least first and second light filtering portions are preferably effectively stacked.

Each of the at least first and second light energy filtering portions may comprise opposing edge portions. The opposing edge portions beneficially face each other. Each of the opposing edge portions beneficially comprise a face. The depth or thickness of the edge portions preferably define the thickness of the at least first and second filter portions respectively.

The opposing edge portions beneficially abut.

The at least first and second light filtering portions are beneficially positioned orthogonal to the energy pathway. The at least first and second light energy filtering portions may each comprise a major face facing the light energy emitted from the light emitting source.

The major face of the at least first and second light energy filtering portions are beneficially substantially planer. The major face of the at least first and second light energy filtering portions are beneficially co-planar.

The major face of the at least first and second light energy filtering portions are beneficially substantially symmetrical about the opposing edge portions.

The energy pathway is beneficially defined by a cross-sectional length extending between opposing side walls and a width defined between opposing upper and lower walls, and where the length is greater than the width, and where the at least first and second light energy filtering portions span between the opposing side walls.

It is preferred that the longitudinal length of the at least first and second filter portion is greater than the width. The opposing edge portions beneficially extend between opposing side walls.

The light energy emitted from the light source beneficially diverges outwardly and tends to have an energy profile in an axis transverse to the energy pathway that reduces both sides of a maximum energy value, and where the apparatus is arranged such that the light having the maximum energy value contacts a region of the filter arrangement comprising the opposing edge portions.

It has been found that there is a thermal profile associated with the light energy where the maximum concentration of light energy produces the greatest temperature at the filter arrangement. As such, the light energy should be focused upon the opposing edge portions of the first and second light energy filtering portions to minimise the chance of the first and second filter portions cracking.

The filter arrangement is preferably retained in the housing.

The filter arrangement may be retained in a fixed position in the housing.

The apparatus is beneficially portable and handheld.

The filter arrangement preferably comprises a frame for receipt and retaining of the at least first and second light energy filtering portions in a fixed relative position.

The first and second light energy filtering portions may further comprise a dichroic coating.

The present invention will now be described by way of example only with reference to the accompanying drawings in which.

FIGS. 3a-d are schematic representations of filter arrangements according to an exemplary embodiment of the present invention.

Figure 1:
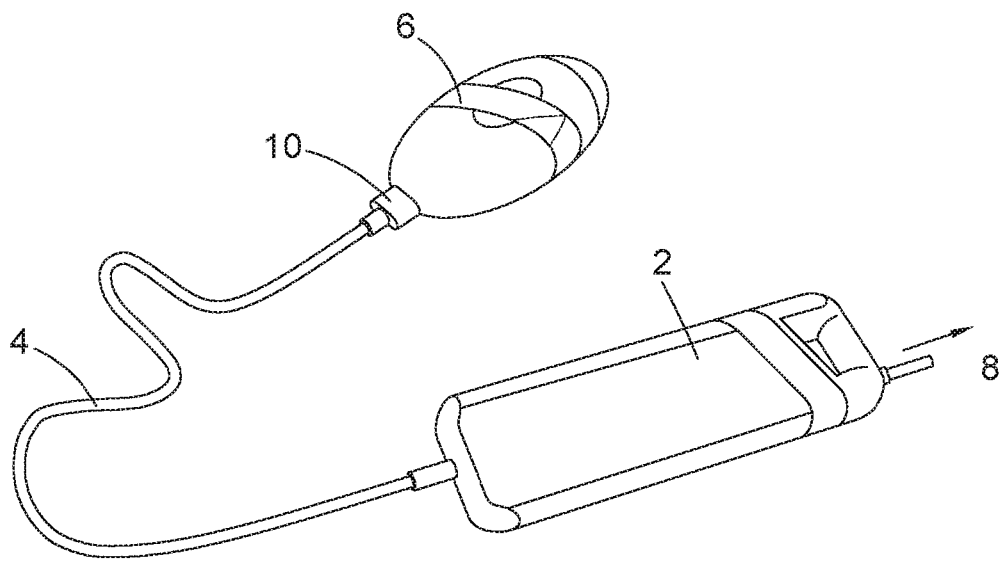
FIG. 1 is a schematic perspective view of an apparatus according to an exemplary embodiment of the present invention.

Referring to FIG. 1 there is a schematic representation of an apparatus according to an exemplary embodiment of the present invention. The apparatus presented is an Intense Pulse Light (IPL) device comprising a handset (6) connected via an umbilical cable (4) to a charging module (2). The charging module (2) in turn is connected to a mains power supply represented by arrow (8).

Figure 2:
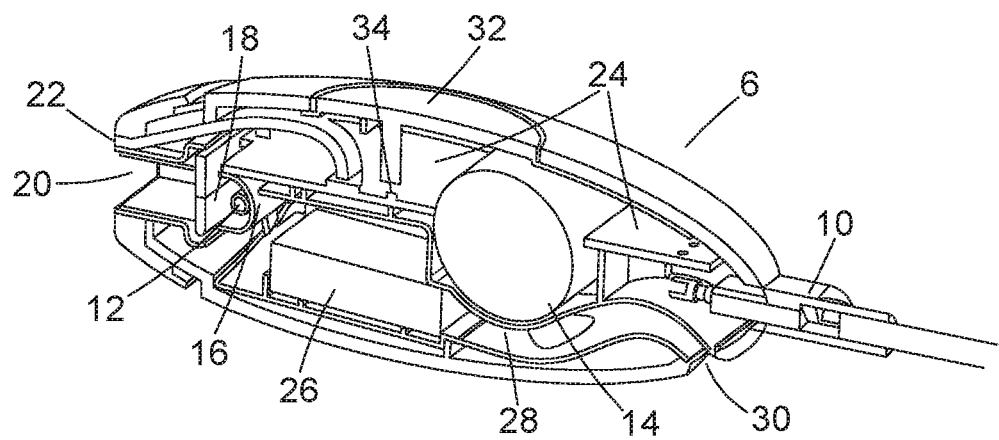
FIG. 2 is a schematic cross sectional perspective view of a handset according to an exemplary embodiment of the present invention.

Referring to FIG. 2 there is a cross-section through the handset (6) presenting the components of the handset according to an exemplary embodiment. The handset (6) comprises a connector (10) for connection to the charging module (2). A flash lamp in the form of a xenon flash lamp (12) is provided and is driven by the storage capacitor (14). Light output from the lamp (12) is focused by reflector (16) forwardly through filter arrangement (18). The filter may be a high pass filter with a cut on wavelength in the range of 470 nm to 650 nm. Typically the filter has a cut on of approximately 510 nm to ensure harmful lower wavelengths cannot pass to the skin.

The light energy having passed through the filter (18) is output of the device from the mouth (20). One or more of a skin contact/skin tone sensor (22) is provided that the forward end of the handset adjacent to the mouth (20). Such a skin contact/tone sensor (22) is in communication with the controller taking the form of a control PCB (24) to prevent operation of the apparatus unless a valid skin contact/tone reading is received.

Due to the significant amount of heat generated by the lamp (12) a cooling fan (26) is provided to draw air into the handset thereby cooling the lamp. Hot air is output through the air duct (28) and exits the handset from outlet (30). Further components comprise a user operable actuator in the form of a button (32) to cause operation of the device and there is further provided a skin contact indicator light (34) indicating that the forward end of the handset is in contact or is in proximity to the skin.

The filter arrangement is shown in FIG. 2 and is provided in the energy pathway that extends between the lamp (12) and the mouth (20). The filter arrangement (18) can be seen to be positioned in the energy pathway and has, in the exemplary embodiment, first and second light energy filtering portions (18a, 18b) together combining to span across the energy pathway for filtering the light energy passing to external of the apparatus. Additional light energy filtering portions may be utilised. By increasing the number of filter portions each portion is effectively reduced in size and thus for the same input from the flashlamp each filter portion undergoes less thermal stress.

Figure 3A:
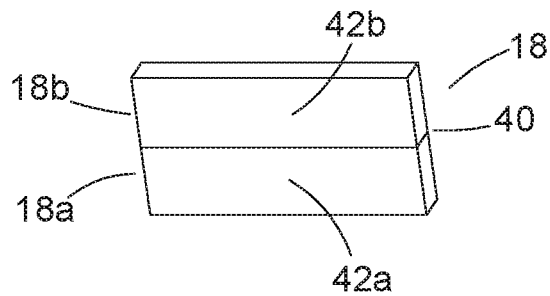

Referring to FIG. 3a a first and a second light energy filtering portion (18a, 18b) are presented. The first and second light filtering portions (18a, 18b) are shown in a side by side configuration whereby the second light energy filtering portion is stacked on top of the first light energy filtering portion (18a). The first and second light energy filtering portions (18a, 18b) are shown to be abutting whereby opposing edge portions effectively face each other and abut against one another. The opposing edge portions are shown abutting at reference number (40). The first and second light filtering portions (18a, 18b) provide major faces respectively (42a, 42b) forming a forward face for facing the light energy emitted from the light emitting source. Together the face (42) is substantially planar. The filter arrangement (18) may be symmetrical about the abutment line (40). Additionally and importantly, however, it is beneficial that the maximum energy associated with the emitted light energy is focused upon the abutment line between the first and second light filtering portion (18a, 18b). The thermal profile associated with the light energy emitted from the light source (12) tends to have an energy profile that reduces outwardly from a maximum energy value. Accordingly, a similar thermal profile is also apparent and by ensuring that the maximum temperature light energy is focused upon the interruption between the opposing edge portions the light filtering portions (18a, 18b) the thermally induced stress is reduced.

Figure 3B:
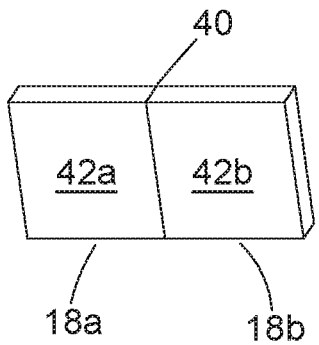

It will be appreciated that the first and second light filtering portions (18a, 18b) must be close enough to each other to prevent unfiltered light energy passing between them. Referring to FIG. 3b, it will be appreciated that the filter arrangement may be configured such that the first and second light filtering portion are positioned in a side by side configuration relative to the top and bottom of the handset (6). In such an embodiment, however, where the width is greater than the height, thermally induced stress is reduced albeit effectiveness is less than in the embodiment shown in FIG. 3a.

Figure 3C:
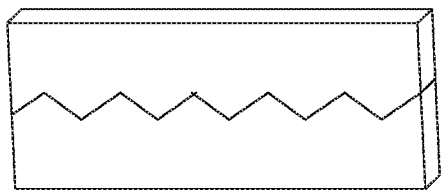

Referring to FIG. 3c, a further embodiment is presented. In this embodiment the opposing edge portions are non-planar which may further reduce thermally induced stresses allowing operation at higher energy throughput.

Figure 3D:
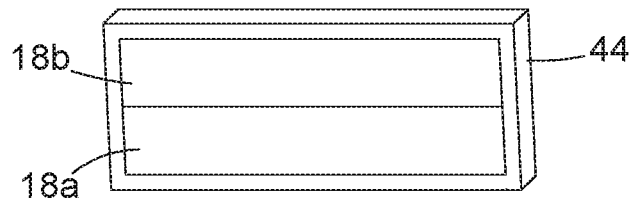

Referring to FIG. 3d the embodiment as presented in FIGS. 3a-c is shown whereby the first and second light filtering portions (18a, 18b) are retained in a housing or frame (44) in order to aid assembly.

The present invention has been described by way of example only and it will be appreciated to the skilled addressee that modification and variations may be made without departing from the scope of protection afforded by the appended claims.

The invention claimed is:

1. A light emitting apparatus for providing dermatological treatment comprising:
   a housing;

a light emitting source provided in the housing and configured to emit light energy along an energy pathway to external of the apparatus; and a filter arrangement retained in a fixed position in the housing and comprising at least a first and a second light energy filtering portion positioned in a side by side configuration;

wherein each of the at least first and second light energy filtering portions comprise opposing edge portions that face each other and abut;

wherein the at least first and second light energy filtering portions together combine to span across the energy pathway; and wherein the at least first and second light energy filtering portions are configured to:
  filter the light energy passing to external of the apparatus; and
  emit the same spectral output.

2. The light emitting apparatus according to claim 1, wherein the light filtering portions have a cut-on value in the range of 470 to 650 nm.

3. The light emitting apparatus according to claim 1, wherein the apparatus an intense pulsed light (IPL) apparatus.

4. The light emitting apparatus according to claim 1, wherein the at least first and second light filtering portions are positioned orthogonal to the energy pathway.

5. The light emitting apparatus according to claim 1, wherein the at least first and second light energy filtering portions comprise a major face facing the light energy emitted from the light emitting source.

6. The light emitting apparatus according to claim 5, wherein the major face of the at least first and the second light energy filtering portions are substantially planar.

7. The light emitting apparatus according to claim 1, wherein the housing comprises an upper wall, a lower wall, and opposing side walls;
  wherein the energy pathway is defined by:
    a cross-sectional length extending between the opposing side walls of the housing; and
    a width defined between the upper and lower walls of the housing;
  wherein the length is greater than the width; and
  wherein the at least first and second light energy filtering portions span between the opposing side walls of the housing.

8. The light emitting apparatus according to claim 1, wherein the light energy emitted from the light source that diverges outwardly tends to have an energy profile in an axis transverse to the energy pathway that reduces on both sides of a maximum energy value; and
  wherein the apparatus is arranged such that the light energy having the maximum energy value contacts a region of the filter arrangement comprising the opposing edge portions.

9. The light emitting apparatus according to claim 1 further comprising a frame for receipt and retaining of the first and second light energy filtering portions in the fixed relative position.

10. The light emitting apparatus according to claim 1, wherein the light emitting source emits white light.

11. The light emitting apparatus according to claim 1, wherein the light emitting source is a xenon flashlamp.

12. The light emitting apparatus according to claim 1, wherein the light filtering portions have a cut-on value of approximately 510 nm.

13. The light emitting apparatus according to claim 5, wherein the major face of the first and the second light energy filtering portions are co-planar.

14. A light emitting apparatus for providing dermatological treatment comprising:
  a housing;
  a light emitting source within the housing and is configured to emit light energy along an energy pathway external the apparatus; and
  a filter arrangement retained in a fixed position in the housing and positioned in the energy pathway;
  wherein the filter arrangement comprises at least a first light energy filtering portion and a second light energy filtering portion, each portion comprising opposing edge portions that face each other and abut;
  wherein each of the at least first and second light energy filtering portions have the same cut-on value, the cut-on value being in the range of 470 to 650 nm; and
  wherein the at least first and second light energy filtering portions are configured to:
    filter the light energy; and
    emit the same spectral output.

15. The light emitting apparatus according to claim 14, wherein the apparatus is an intense pulsed light (IPL) apparatus.

16. The light emitting apparatus according to claim 14, wherein the housing comprises an upper wall, a lower wall, and opposing side walls;
  wherein the energy pathway is defined by:
    a cross-sectional length extending between the opposing side walls of the housing; and
    a width defined between the upper and lower walls of the housing;
  wherein the length is greater than the width; and
  wherein the at least first and second light energy filtering portions span between the opposing side walls of the housing.

17. The light emitting apparatus according to claim 14, wherein the light energy emitted from the light source that diverges outwardly tends to have an energy profile in an axis transverse to the energy pathway that reduces on both sides of a maximum energy value; and
  wherein the apparatus is arranged such that the light energy having the maximum energy value contacts a region of the filter arrangement comprising the opposing edge portions.

18. The light emitting apparatus according to claim 14 further comprising a frame for receipt and retaining of the first and second light energy filtering portions in the fixed relative position.

19. The light emitting apparatus according to claim 14, wherein the light emitting source is a xenon flashlamp.

20. The light emitting apparatus according to claim 14, wherein the light filtering portions have a cut-on value of approximately 510 nm.

* * * * *